United States Patent [19]

Richelsoph et al.

[11] Patent Number: 5,683,392
[45] Date of Patent: Nov. 4, 1997

[54] MULTI-PLANAR LOCKING MECHANISM FOR BONE FIXATION

[75] Inventors: Marc E. Richelsoph, Bartlett; Eric C. Lange; Maureen J. Theis, both of Cordova, all of Tenn.

[73] Assignee: Wright Medical Technology, Inc., Arlington, Tenn.

[21] Appl. No.: 543,977

[22] Filed: Oct. 17, 1995

[51] Int. Cl.$^6$ .................................. A61B 17/70
[52] U.S. Cl. .................. 606/61; 606/60; 606/72
[58] Field of Search .................. 606/61, 60, 69, 606/72, 73

[56] References Cited

U.S. PATENT DOCUMENTS

| | | | |
|---|---|---|---|
| 4,946,458 | 8/1990 | Harms et al. | |
| 5,002,542 | 3/1991 | Frigg | 5/4 |
| 5,047,029 | 9/1991 | Aebi et al. | 17/58 |
| 5,196,013 | 3/1993 | Harms et al. | 5/4 |
| 5,443,467 | 8/1995 | Biedermann et al. | 606/65 |
| 5,549,608 | 8/1996 | Errico et al. | 17/70 |

Primary Examiner—Michael Buiz
Assistant Examiner—Daphna Shal
Attorney, Agent, or Firm—Walker, McKenzie & Walker, P.C.

[57] ABSTRACT

A locking mechanism for locking a rod to a bone member. The locking mechanism includes a bone fixation member for attachment to the bone member, the bone fixation member having a spherical portion; an inner housing member having a channel for receiving the rod and having a spherical portion for engaging the spherical portion of the bone fixation member; and an outer housing member for locking the inner housing member to the rod and the spherical portion of the bone fixation member.

10 Claims, 4 Drawing Sheets

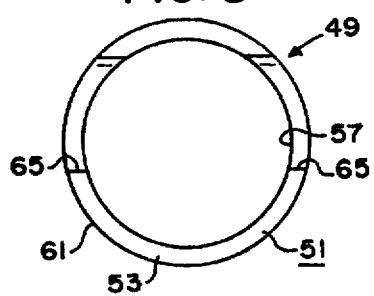
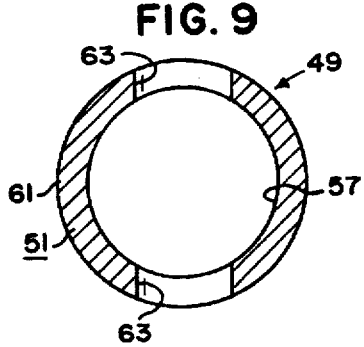
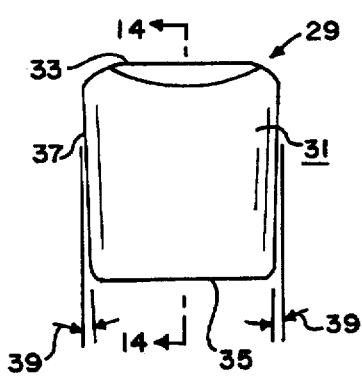
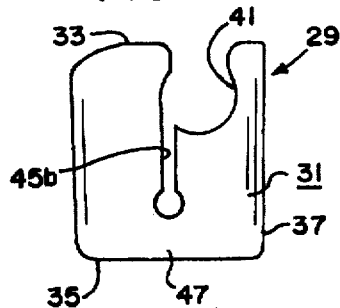
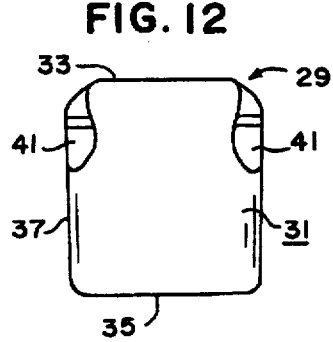
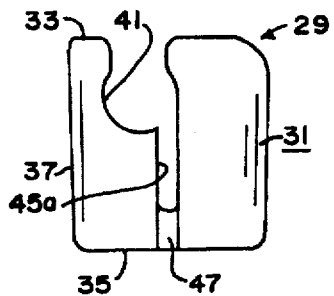
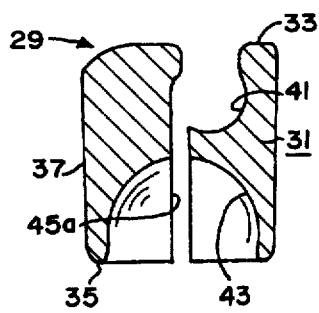
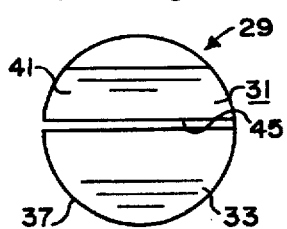
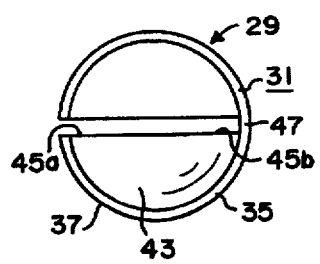

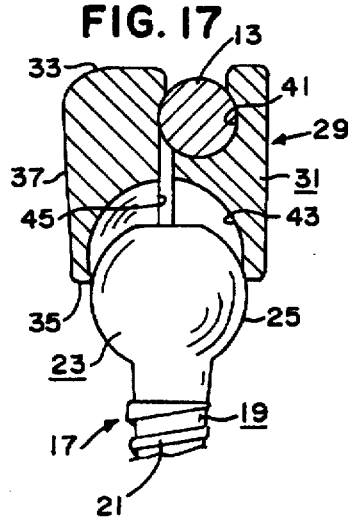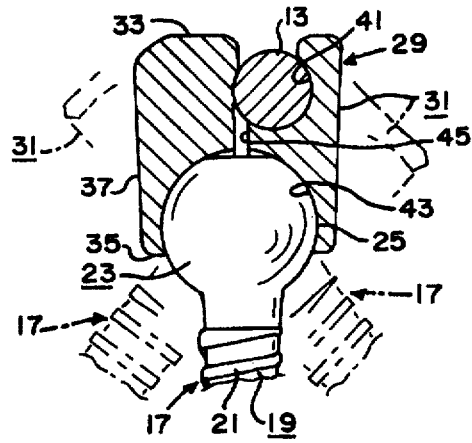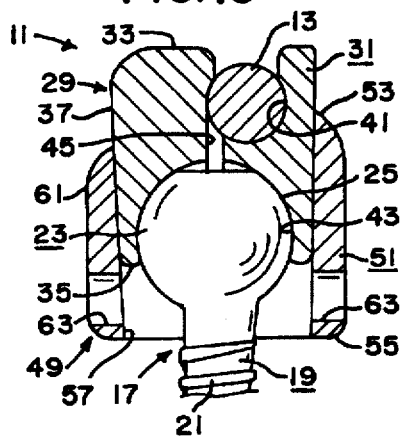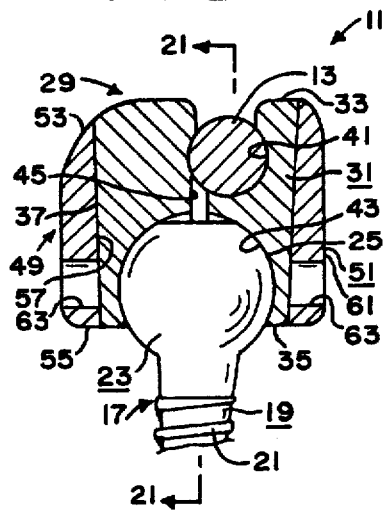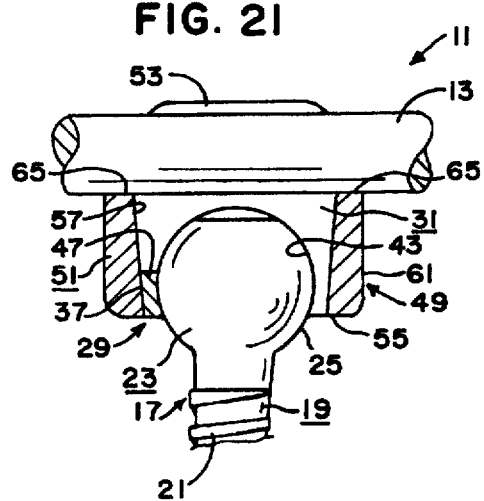

MULTI-PLANAR LOCKING MECHANISM FOR BONE FIXATION

BACKGROUND OF THE INVENTION

1. Field of the Invention

The present invention relates, in general, to a locking mechanism for locking a rod to a bone member and, more specifically, to multi-planar locking mechanism for securing a rod to a vertebra.

2. Background Art

In spine surgery, it is often difficult and time consuming to lock a spinal rod to the fixated hooks and/or screws. Many locking mechanism for locking a spinal rod to fixation hook and/or screws do not offer the variability to make this an easy task. To compensate for this short-coming, the spinal rod must be contoured to allow for the multi-planar variability that exists between vertebral levels.

Nothing in the known prior art discloses or suggests the present invention. More specifically, nothing in the known prior art discloses or suggests a locking mechanism including a bone fixation member for attachment to a bone member, the bone fixation member having a spherical portion; an inner housing member having a channel for receiving a rod and having a spherical portion for engaging the spherical portion of the bone fixation member; and an outer housing member for locking the inner housing member to the rod and the spherical portion of the bone fixation member.

SUMMARY OF THE INVENTION

The present invention provides a multi-planar locking mechanism for locking a rod to a bone fixation device such as a bone screw or hook. The multi-planar of the present invention provides, in general, a non-set screw, multi-planar locking mechanism that can be adapted for both spinal hooks and screws. The multi-planar capability decreases overall operative time by decreasing the need for intra-operative rod contouring, and increasing the ease of implant assembly. This locking mechanism allows up to 20 degrees or more of screw/hook angulation in all planes relative to the rod. The lock is fastened through a taper interface which, when engaged, compresses an inner sleeve/housing member about both the rod and hook/screw, securing the assembly position. The locking mechanism is top-loading and fully reversible. There are several designs for which this concept could be applicable: (1) An inner housing member snaps onto both the spherical head portion of a hook/screw and onto the rod. Variability in all planes is offered until the outer housing member, with a tapered inside wall, is pulled up and interfaces with the tapered walls of the inner housing member.

The locking mechanism of the present invention includes, in general, a bone fixation member for attachment to a bone member, the bone fixation member having a spherical portion; an inner housing member having a channel for receiving a rod and having a spherical portion for engaging the spherical portion of the bone fixation member; and an outer housing member for locking the inner housing member to the rod and the spherical portion of the bone fixation member.

One object of the present invention is to provide a multi-planar locking mechanism that can be adapted for both spinal hooks and screws.

Another object of the present invention is to provide such a multi-planar locking mechanism that deceases overall operative time by decreasing the need for intra-operative rod contouring, and increases the ease of implant assembly.

Another object of the present invention is to provide such a multi-planar locking mechanism that allows up to 20 degrees or more of screw/hook angulation in all planes relative to the rod.

Another object of the present invention is to provide such a multi-planar locking mechanism that is top-locking and fully reversible.

BRIEF DESCRIPTION OF THE DRAWINGS

FIG. 8 is a top plan view of the outer housing member of FIG. 4.

FIG. 9 is a sectional view substantially as taken on line 9—9 of FIG. 4.

FIG. 10 is a front elevational view of an inner housing member of the locking mechanism of the present invention.

FIG. 11 is a right side elevational view of the inner housing member of FIG. 10.

FIG. 12 is a rear elevational view of the inner housing member of FIG. 10.

FIG. 13 is a left side elevational view of the inner housing member of FIG. 10.

FIG. 14 is a sectional view substantially as taken on line 14—14 of FIG. 10.

FIG. 15 is a top plan view of the inner housing member of FIG. 10.

FIG. 16 is a bottom plan view of the inner housing member of FIG. 10.

FIG. 17 is a somewhat diagrammatic view showing a head portion of the bone fixation member of FIG. 2 being positioned into a cavity of the inner housing member of FIG. 10, and showing a rod positioned in channel of the inner housing member.

FIG. 18 is substantially similar to FIG. 17 but shows the head portion of the bone fixation member fully positioned in the cavity of the inner housing member.

FIG. 19 is substantially similar to FIG. 18 but shows the outer housing member of FIG. 4 being positioned onto the inner housing member.

FIG. 20 is substantially similar to FIG. 19 but shows the outer housing member fully positioned on the inner housing member, causing the bone fixation member and the rod to be securely and non-movably locked relative to one another.

FIG. 21 is a sectional view substantially as taken on line 21—21 of FIG. 20.

DESCRIPTION OF THE PREFERRED EMBODIMENTS

Figure 1:
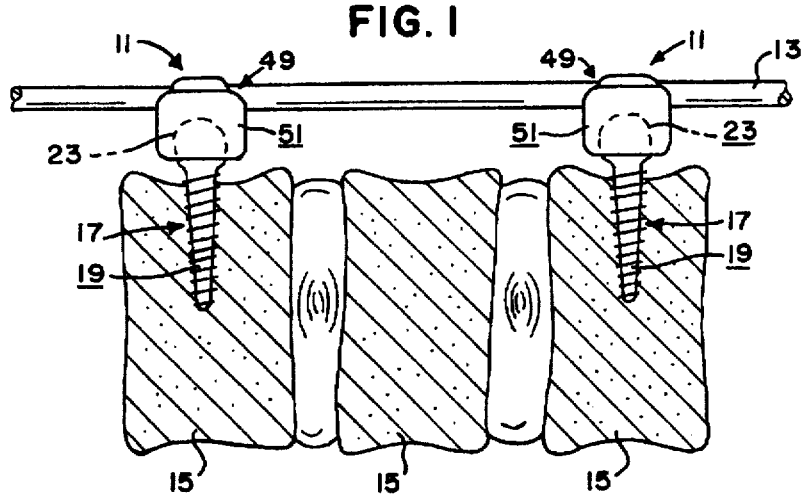
FIG. 1 is a somewhat diagrammatic view of a plurality of locking mechanisms of the present invention shown locking an elongated rod to a plurality of bone members.
Figure 2:
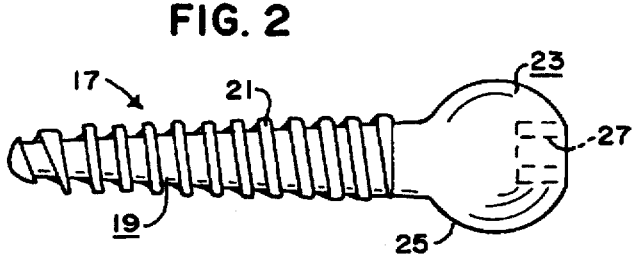
FIG. 2 is an elevational view of a bone fixation member of the locking mechanism of the present invention.
Figure 3:
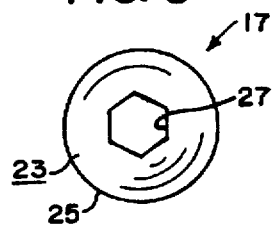
FIG. 3 is an end view of the bone fixation member of FIG. 2.
Figure 4:
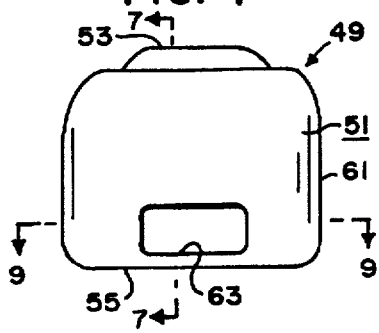
FIG. 4 is a front elevational view of an outer housing member of the locking mechanism of the present invention.
Figure 5:
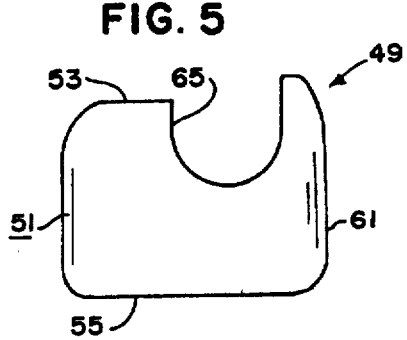
FIG. 5 is a side elevational view of the outer housing member of FIG. 4.
Figure 6:
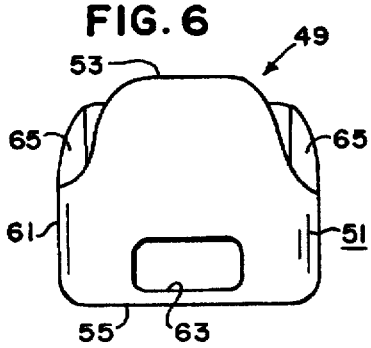
FIG. 6 is a rear elevational view of the outer housing member of FIG. 4.
Figure 7:
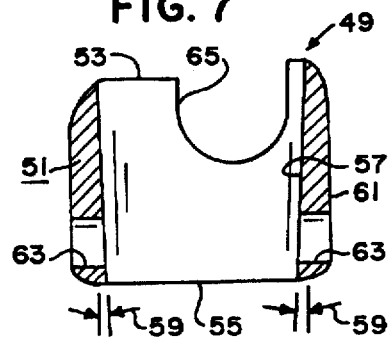
FIG. 7 is a sectional view substantially as taken on line 7—7 of FIG. 4.
Figure 22:
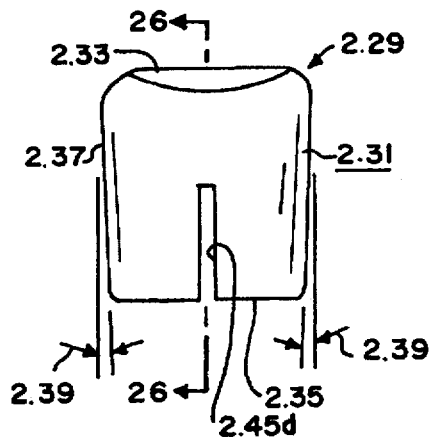
FIG. 22 is a front elevational view of a modified embodiment of the inner housing member of the locking mechanism of the present invention.
Figure 23:
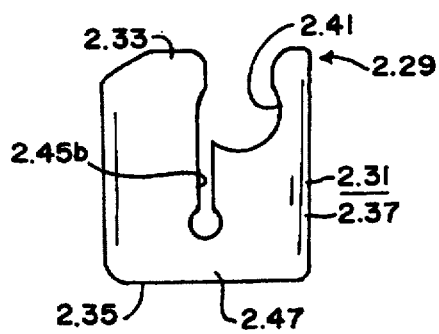
FIG. 23 is a right side elevational view of the inner housing member of FIG. 22.
Figure 24:
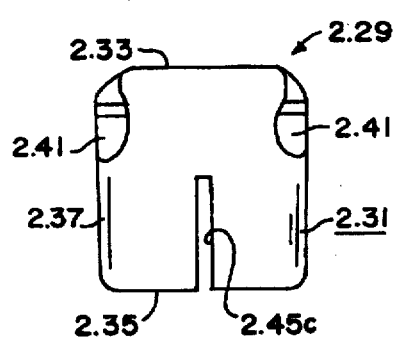
FIG. 24 is a rear elevational view of the inner housing member of FIG. 22.
Figure 25:
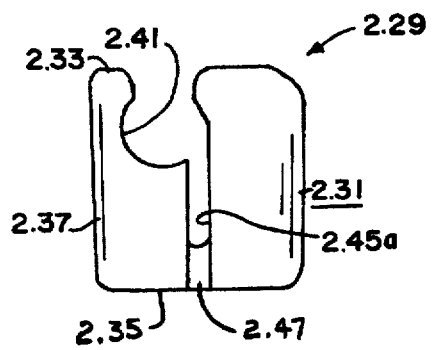
FIG. 25 is a left side elevational view of the inner housing member of FIG. 22.
Figure 26:
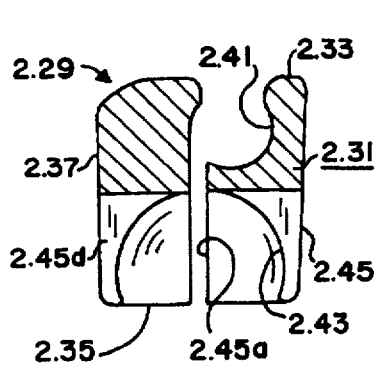
FIG. 26 is a sectional view substantially as taken on line 26—26 of FIG. 22.
Figure 27:
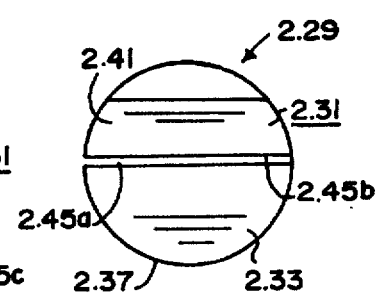
FIG. 27 is a top plan view of the inner housing member of FIG. 22.
Figure 28:
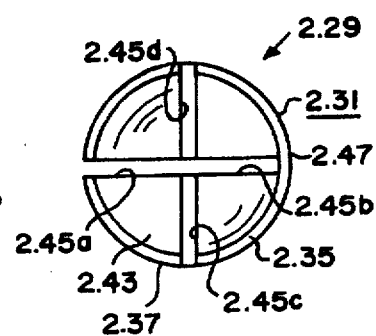
FIG. 28 is a bottom plan view of the inner housing member of FIG. 22.

A first preferred embodiment of the multi-planar locking mechanism of the present invention is shown in FIGS. 1–21, and identified by the numeral 11. The locking mechanism 11 is specifically designed to lock a substantially rigid, elongated rod 13 relative to a bone member 15. A pair of locking mechanisms 11 are shown in FIG. 1 locking a rod 13 to a spaced pair of bone members 15.

The locking mechanism 11 includes a bone fixation member 17 (see, in general, FIGS. 2 and 3) adapted to be fixed to a bone member 15. The bone fixation member 17 includes a bone attachment portion 19 adapted to be attached to the bone member 15. The bone attachment portion 19 may include external bone screw threads 21 adapted to be screwed into the bone member 15. The screw threads 21 may be of any specific design, pitch, etc., now apparent to those skilled in the art for being screwed into and secured to bone. The bone fixation member 17 includes a head portion 23 attached to the bone attachment portion 19. The head portion 23 has a substantially spherical outer surface 25. The head portion 23 may include means for allowing the bone attachment portion 19 to be easily attached into the bone member 15 with the aid of a tool. Thus, the head portion 23 may include a hexagonal-shaped socket 27 for allowing a tool such as a screw driver or the like having a hexagonal-shaped drive end to be used to drive and screw the screw threads 21 into the bone member 15 to thereby attach the bone fixation member 17 into the bone member 15 as will now be apparent to those skilled in the art.

The bone fixation member 17 may be manufactured out of various materials and in various manners. Thus, for example, the bone fixation member 17 may be machined out of a surgical grade stainless steel or the like. The bone fixation member 17 may be manufactured in various sizes depending on the specific bone member 15 it is to be fixed to, etc. Thus, for example, for a lower back vertebra, the screw threads 21 may have a length of approximately 1 inch (2.24 centimeters) and the head portion 23 may have a diameter of approximately 0.375 inch (approximately 1.48 centimeters).

The locking mechanism 11 includes an inner housing member or sleeve 29 (see, in general, FIGS. 10–16) adapted to engage the rod 13 and the head portion 23 of the bone fixation member 17. The inner housing member 29 preferably includes a body 31 having a first end 33, a second end 35, and a substantially cylindrical outer surface 37. The outer surface 37 is tapered between the first and second ends 33, 35. The angle of taper 39 of the outer surface (see FIG. 10) may be approximately 3 degrees. The first end 33 of the body 31 has a channel 41 extending thereacross for receiving the rod 13. The channel 41 includes a contour having a cross sectional area that substantially matches a portion of the cross sectional area of the contour of the rod 13 as clearly shown in FIGS. 17–20. The second end 35 of the body 31 has a cavity 43 therein for receiving the head portion 23 of the bone fixation member 17. The cavity 43 includes a contour having a cross sectional area that substantially matches a portion of the cross sectional area of the contour of the substantially spherical outer surface 25 of the head portion 23 as clearly shown in FIGS. 17–20. The cavity 43 has a substantially spherical surface that is preferably slightly greater than a hemisphere so that the width of the mouth thereof is slightly less than the maximum diameter thereof whereby the head portion 23 can be "snapped" into the cavity 43 as shown in FIGS. 17 and 18. The body 31 preferably has a first slot 45a communicating with the cavity 43 and with the channel 41 for allowing the body 31 to be easily compressed about the substantially spherical outer surface 25 of the head portion 23 of the bone fixation member 17 and the rod 13 in a manner as will hereinafter become apparent. Further, the body 31 preferably has a second slot 45b communicating with a portion of the cavity 43 and with the channel 41 for allowing the body 31 to be more easily compressed about the substantially spherical outer surface 25 of the head portion 23 of the bone fixation member 17 and the rod 13 in a manner as will hereinafter become apparent. As clearly shown in FIG. 16, the second slot 45b is positioned substantially 180 degrees from the first slot 45a. The first slot 45a extends completely between the first and second ends 33, 35 of the body 31 while the second slot 45b extends between the first and second ends 33, 35 through all but a portion 47 of the body 31 thereby effectively dividing the body 31 into two parts joined together by the portion 47 which forms and functions as a hinge joining the two parts of the body 31 together.

The inner housing member 29 may be manufactured out of various materials and in various manners. Thus, for example, the inner housing member 29 may be machined out of a surgical grade stainless steel or the like. The inner housing member 29 may be manufactured in various sizes depending on the rod 13 and bone fixation member 17 it is to be fixed to, etc.

The locking mechanism 11 includes an outer housing member or cap 49 (see, in general, FIGS. 4–9) adapted to engage the outer surface 37 of the body 31 of the inner housing member 29. The outer housing member 49 preferably includes a body 51 having a first end 53, a second end 55, and a substantially cylindrical passageway 57 extending therethrough along the longitudinal axis thereof. The passageway 57 is tapered between the first and second ends 53, 55 of the body 51 an amount substantially equal to the taper of the outer surface 37 of the body 31 of the inner housing member 29. Thus, the angle of taper 59 of the passageway 57 (see FIG. 7) may be approximately 3 degrees. The passageway 57 is sized so that the first end 53 of the body 51 of the outer housing member 49 can be inserted onto the second end 35 of the body 31 of the inner housing member 29 as clearly shown in FIG. 19. The passageway 57 includes a contour having a cross sectional area that substantially matches but is slightly smaller than the non-compressed cross sectional area of the contour of the outer surface 37 of the inner housing member 29 so that when the outer housing member 49 is forced substantially completely over the inner housing member 29 (or, vice versa, when the inner housing member 29 is forced substantially completely into the passageway 57) as clearly shown in FIGS. 20 and 21, the inner housing member 29 will be "compressed" about the rod 13 and the head portion 23 of the bone fixation member 17 to securely and non-movably lock the rod 13 and the bone fixation member 17 relative to one another as will now be apparent to those skilled in the art. The body 51 preferably has an outer surface 61 with one or more notches or openings 63 therein for allowing a tool such as a pair of pliers or the like (not shown) to be used to force the inner and outer housing members 29, 49 together to the position shown in FIGS. 20 and 21. The body 51 may have a channel 65 across the first end 53 thereof to provide clearance for the rod 13 when the inner and outer housing members 29, 49 are forced to the position shown in FIGS. 20 and 21.

The outer housing member 49 may be manufactured out of various materials and in various manners. Thus, for example, the outer housing member 49 may be machined out of a surgical grade stainless steel or the like. The outer housing member 49 may be manufactured in various sizes depending on the size of the inner housing member 29 it is to be fixed to, etc.

The method of locking a rod 13 relative to a bone member 15 using the locking mechanism 11 of the present invention may begin with a surgeon deciding on a desired location of the rod 13 with respect to one or more bone members 15. A portion of a bone member 15 may be exposed and a bone fixation member 17 may be secured thereto with the head portion 23 located based primarily on the best location for securing the bone attachment portion 19 to the bone member 15 rather than an attempt to have the rod 13 and bone fixation member 17 substantially align with one another in the same plane, etc. Once the bone fixation member 17 is properly secured to the bone member 15 by, for example, screwing the screw threads 21 of the bone attachment portion 19 of the bone fixation member 17 into the bone member 13 as shown in FIG. 1, the outer housing member 49 can be positioned over the head portion 23. With the rod 13 inserted into the channel 41 of the first end 33 of the body 31 of the inner housing member 29, the cavity 43 in the body 31 of the inner housing member 29 can then be pressed or snapped onto the head portion 23 of the bone fixation member 17 as shown in FIGS. 17 and 18. Variability between the rod 13 and the bone fixation member 17 is allowed in all planes. Thus, the inner housing member 13 as shown rotated about the longitudinal axis of the rod 13 as shown in broken lines in FIG. 18 and the head portion 23 of the bone fixation member 17 can be moved within the cavity 43 in the body 31 of the inner housing member 29 through the a range of angulation up to 20 degrees or more as indicated in broken lines in FIG. 18 in all planes relative to the rod 13, and rotated 360 degrees about the axis of the cavity 43 in all planes relative to the rod 13. Such variability allows the surgeon to easily connect the rod 13 to the head portion 23 of the bone fixation member 17 at the optimum or desired planar interface, etc. Once the rod 13 and head portion 23 are so positioned, the outer housing member 49 is merely pulled or pushed over the inner housing member 29 as shown in FIGS. 19 and 20, compressing or forcing the channel 41 in the first end 33 of the body 31 of the inner housing member 29 about the rod 13 and compressing or forcing the cavity 43 in the second end 35 of the body 31 of the inner housing member 29 about the head portion 23 of the bone fixation member 17, thereby securely and non-movably locking the rod 13 relative to the bone fixation member 17 and bone member 15 as will now be apparent to those skilled in the art.

A modified embodiment of the inner housing member or sleeve of the locking mechanism 11 of the present invention is shown in FIGS. 22–28 and identified by the numeral 2.29. The inner housing member 2.29 preferably includes a body 2.31 having a first end 2.33, a second end 2.35, and a substantially cylindrical outer surface 2.37. The outer surface 2.37 is tapered between the first and second ends 2.33, 2.35. The angle of taper 2.39 of the outer surface (see FIG. 22) may be approximately 3 degrees. The first end 2.33 of the body 2.31 has a channel 2.41 extending thereacross for receiving the rod 13. The channel 2.41 includes a contour having a cross sectional area that substantially matches a portion of the cross sectional area of the contour of the rod 13. The second end 2.35 of the body 2.31 has a cavity 2.43 therein for receiving the head portion 23 of the bone fixation member 17. The cavity 2.43 includes a contour having a cross sectional area that substantially matches a portion of the cross sectional area of the contour of the substantially spherical outer surface 25 of the head portion 23. The cavity 2.43 has a substantially spherical surface that is preferably slightly greater than a hemisphere so that the width of the mouth thereof is slightly less than the maximum diameter thereof whereby the head portion 23 can be "snapped" into the cavity 2.43. The body 2.31 preferably has a slot communicating with the cavity 2.43 for allowing the body 2.31 to be easily compressed about the substantially spherical outer surface 25 of the head portion 23 of the bone fixation member 17 when the body 2.31 is received in the passageway 57 of the body 51 of the outer housing member 49, and preferably has a slot communicating with the channel 2.41 for allowing the body 2.31 to be easily compressed about the rod 13 when the body 2.31 of the inner housing member 2.29 is received in the passageway 57 of the body 51 of the outer housing member 49. More specifically, the body 2.31 preferably has a first slot 2.45a communicating with the cavity 2.43 and with the channel 2.41 for allowing the body 2.31 to be easily compressed about the substantially spherical outer surface 25 of the head portion 23 of the bone fixation member 17 and about the rod 13 when the body 2.31 of the inner housing member 2.29 is received in the passageway 57 of the body 51 of the outer housing member 49. Further, the body 2.31 preferably has a second slot 2.45b communicating with a portion of the cavity 2.43 and with the channel 2.41 for allowing the body 2.31 to be more easily compressed about the substantially spherical outer surface 25 of the head portion 23 of the bone fixation member 17 and about the rod 13 when the body 2.31 of the inner housing member 2.29 is received in the passageway 57 of the body 51 of the outer housing member 49. As clearly shown in FIG. 28, the second slot 2.45b is positioned substantially 180 degrees from the first slot 2.45a. The first slot 2.45a extends completely between the first and second ends 2.33, 2.35 of the body 2.31 while the second slot 2.45b extends between the first and second ends 2.33, 2.35 through all but a portion 2.47 of the body 2.31 thereby effectively dividing the body 2.31 into two parts joined together by the portion 2.47 which forms and functions as a hinge joining the two parts of the body 2.31 together.

In addition, the body 2.31 preferably has a third slot 2.45c and a fourth slot 2.45d both communicating with a portion of the cavity 2.43 for allowing the body 2.31 to be more easily compressed about the substantially spherical outer surface 25 of the head portion 23 of the bone fixation member 17 when the body 2.31 of the inner housing member 2.29 is received in the passageway 57 of the body 51 of the outer housing member 49. As clearly shown in FIG. 28, the third slot 2.45c is positioned substantially 90 degrees from the first slot 2.45a and substantially 180 degrees from the fourth slot 2.45d.

The inner housing member 2.29 may be manufactured out of various materials and in various manners. Thus, for example, the inner housing member 2.29 may be machined out of a surgical grade stainless steel or the like. The inner housing member 2.29 may be manufactured in various sizes depending on the rod 13 and bone fixation member 17 it is to be fixed to, etc.

The function and operation of the inner housing member 2.29 is substantially similar to that of the inner housing member 29 and the above disclosure of the function and operation of the inner housing member 29 should be consulted for a more complete understanding of the function and operation of the inner housing member 2.29. The addition of the third and fourth slots 2.45c, 2.45d increases the flexibility of the body 2.31 so that the cavity 2.43 can be more easily compressed about the substantially spherical outer surface 25 of the head portion 23 of the bone fixation member 17 as will now be apparent to those skilled in the art.

Although the present invention has been described and illustrated with respect to preferred embodiments and preferred uses therefor, it is not to be so limited since modifications and changes can be made therein which are within the full intended scope of the invention. Thus, while the first preferred embodiment of the present invention have been shown in FIG. 1 as locking or securing a spinal rod to vertebrae, the present invention can additionally be used to secure fractured portions of a long bone such as a femur, etc., to an external rod for reducing and fixing the fracture, etc. A second preferred embodiment of the locking mechanism of the present invention may include a spherical sleeve or inner housing member for snapping onto the rod which then seats in a spherical indentation on top of a bone screw/hook. This spherical interface allows for variability in all planes until an outer housing member, with a tapered inside wall, is pulled up and interfaces with tapered walls of the bone screw/hook. A third preferred embodiment of the locking mechanism of the present invention may include a spherical sleeve or inner housing member for snapping onto the rod which then seats in a spherical indentation on top of a bone screw/hook. The spherical interface allows for variability in all planes until a cap or outer housing member, with tapered sides, engages with tapered slots on the head portion or top of the bone hook/screw. A fourth preferred embodiment of the present invention also includes a spherical sleeve or inner housing member for snapping onto the rod which then seats in a spherical indentation on top of a bone screw/hook. This spherical interface allows for variability in all planes until a cap or outer housing member, with tapered slots, engages with tapered sides of the bone hook/screw.

We claim:

1. A locking mechanism for locking a rod to a bone member; said locking mechanism comprising:
    (a) a bone fixation member for attachment to the bone member, said bone fixation member having a spherical portion;
    (b) an inner housing member having a channel for receiving the rod and having a spherical portion for engaging said spherical portion of said bone fixation member; and
    (c) an outer housing member for locking said inner housing member to the rod and said spherical portion of said bone fixation member; said outer housing member including a unitary body for positioning about at least a portion of said inner housing member intermediate said channel and said spherical portion of said inner housing member and for simultaneously applying pressure to said inner housing member adjacent said channel and adjacent said spherical portion of said inner housing member for clamping said inner housing member to the rod and to said spherical portion of said bone fixation member.

2. The locking mechanism of claim 1 in which said inner housing member includes a unitary body having a first end, a second end, and a substantially cylindrical outer surface, said outer surface of said body of said inner housing member being tapered between said first and second ends thereof; and in which said body of said outer housing member has a first end, a second end, and a substantially cylindrical passageway therethrough for slidably receiving said body of said inner housing member; said passageway of said body of said outer housing member being tapered between said first and second ends thereof.

3. The locking mechanism of claim 2 in which said spherical portion of said bone fixation member includes a head portion having a substantially spherical outer surface; and in which said body of said inner housing member has a cavity in said second end thereof with a substantially spherical surface for defining said spherical portion thereof and for receiving said substantially spherical outer surface of said head portion of said bone fixation member.

4. The locking mechanism of claim 3 in which said body of said inner housing member has a slot communicating with said cavity thereof for allowing said body of said inner housing member to be compressed about said substantially spherical outer surface of said head portion of said bone fixation member when said body of said inner housing member is received in said passageway of said body of said outer housing member.

5. The locking mechanism of claim 3 in which said body of said inner housing member has a slot communicating with said channel thereof for allowing said body of said inner housing member to be compressed about said rod when said body of said inner housing member is received in said passageway of said body of said outer housing member.

6. The locking mechanism of claim 2 in which said bone fixation member includes a bone attachment portion adapted to be attached to the bone member.

7. The locking mechanism of claim 6 in which said bone attachment portion of said bone fixation member includes external bone screw threads adapted to be screwed into the bone member.

8. The locking mechanism of claim 2 in which said first end of said outer housing member has a channel extending thereacross for receiving the rod.

9. The locking mechanism of claim 2 in which said body of said outer housing has an outer surface with an opening therein for use in forcing said body of said inner housing member into said passageway of said body of said outer housing member.

10. In combination, an elongated rod and a multi-planar locking mechanism for locking said rod to a vertebra; said locking mechanism comprising:
    (a) a bone screw for attachment to the vertebra, said bone screw including a bone screw thread portion adapted to be screwed into the vertebra and including a head portion attached to the bone screw thread portion; said head portion having a substantially spherical outer surface;
    (b) an inner housing member including a body having a first end, a second end, and a substantially cylindrical outer surface; said outer surface of said body of said inner housing member being tapered between said first and second ends thereof; said first end of said body having a channel extending thereacross receiving said rod; said second end of said body having a cavity receiving said head portion of said bone screw; said cavity having a substantially spherical surface that substantially matches a portion of said substantially spherical outer surface of said head portion of said bone screw; said body of said inner housing member having a slot communicating with said cavity and said channel thereof; and (c) an outer housing member locking said inner housing member to said rod and said head portion of said bone screw; said outer housing member comprising a one-piece, integral body having a substantially cylindrical passageway in which said body of said inner housing member is slidably received, a first end applying pressure against said first end of said body of said inner housing member to compress said first end of body of said inner housing member against said rod to lock said rod to said inner housing member, and a second end applying pressure against said second end of said body of said inner housing member to compress said second end of said body of said inner housing member about said head portion of said bone screw to lock said head portion of said bone screw to said inner housing member; said passageway of said body of said outer housing member being tapered between said first and second ends of said body of said outer housing for causing said body of said inner housing member to be compressed about said substantially spherical outer surface of said head portion of said bone screw and about said rod when said body of said inner housing member is received in said passageway of said body of said outer housing member so that said bone screw and said rod are locked to said inner housing member.

\* \* \* \* \*